United States Patent [19]

Campbell et al.

[11] Patent Number: 4,627,853

[45] Date of Patent: Dec. 9, 1986

[54] METHOD OF PRODUCING PROSTHESES FOR REPLACEMENT OF ARTICULAR CARTILAGE AND PROSTHESES SO PRODUCED

[75] Inventors: Todd D. Campbell, Corona; Aws S. Nashef, Costa Mesa, both of Calif.

[73] Assignee: American Hospital Supply Corporation, Evanston, Ill.

[21] Appl. No.: 738,994

[22] Filed: May 29, 1985

[51] Int. Cl.[4] .......................... A61F 2/28; A61F 2/38; A61K 35/32

[52] U.S. Cl. ........................................ 623/16; 623/18; 623/20; 623/66; 623/22; 623/23; 128/92 R; 424/95; 106/122; 106/161

[58] Field of Search ...................... 424/95; 623/15, 16, 623/20, 22, 23; 128/92 C, 92 R, 92 G; 260/112 R, 118, 123.7; 106/122, 161; 433/201

[56] References Cited

U.S. PATENT DOCUMENTS

| | | |
|---|---|---|
| 4,120,730 | 10/1978 | Trojer et al. |
| 4,172,128 | 10/1979 | Thiele et al. ............ 424/95 |
| 4,257,405 | 3/1981 | Colville . |
| 4,277,238 | 7/1981 | Kategiri . |
| 4,309,488 | 1/1982 | Heide et al. |
| 4,330,891 | 5/1982 | Branemark et al. |
| 4,351,069 | 9/1982 | Ballintyn et al. ............ 128/92 C X |
| 4,394,370 | 7/1983 | Jefferies . |
| 4,407,793 | 10/1983 | Akimova et al. |
| 4,440,750 | 4/1984 | Glowacki . |
| 4,472,840 | 9/1984 | Jefferies . |
| 4,485,096 | 11/1984 | Bell . |
| 4,485,097 | 11/1984 | Bell . |

OTHER PUBLICATIONS

Narang et al., *J. Oral Maxillofac. Surg.* (U.S.), vol. 40, No. 3, pp. 133–141, Mar. 1982.
Glowacki et al., *Calcified Tissue International*, vol. 33, pp. 71–76, 1981.
Wittbjer et al., *Scand. J. Plast. Reconstr. Surg.*, vol. 16, pp. 239–244, 1982.
Takagi et al., *Ann. Surg.*, vol. 196, No. 1, pp. 100–109, Jul. 1982.
Gupta et al., *International Orthopaedics*, vol. 6, pp. 79–85, 1982.
Gupta and Tuli, *Acta Orthop. Scand.*, vol. 53, pp. 857–865, 1982.
Gross et al., *Oral Surg.*, vol. 49, No. 1, pp. 21–26, Jan. 1980.
Urist et al., *Proc. Nat'l. Acad. Sci. U.S.A.*, vol. 76, No. 4, pp. 1828–1832, Apr. 1979.

Primary Examiner—Richard J. Apley
Assistant Examiner—Alan W. Cannon
Attorney, Agent, or Firm—Bernard, Rothwell & Brown

[57] ABSTRACT

Prostheses useful for articulating cartilage replacement, and which are attached to host bone without the use of cements, are derived from bone. Allogenic or xenogenic bone segments are machined into the desired shape and differentially demineralized. The completely demineralized portion has a spongy texture similar to natural cartilage, while the non-demineralized portion is a matrix into which adjacent host bone grows, thus anchoring the prosthesis. The prostheses are tanned which renders the material non-antigenic, biocompatible, and stable.

10 Claims, 2 Drawing Figures

METHOD OF PRODUCING PROSTHESES FOR REPLACEMENT OF ARTICULAR CARTILAGE AND PROSTHESES SO PRODUCED

BACKGROUND OF THE INVENTION

Various prostheses have been used for replacement of joints. Replacement is desirable when joints have been damged by disease (including various forms of arthritis and other diseases causing degeneration of cartilage in joints) or injury, including rupture of the cartilage.

Some problems encountered after implantation of such prostheses are caused by the cements used to attach the prosthesis to host bone. The cements have been known to loosen and thus the prosthesis eventually fails. Decomposing cement may also move into the joint itself, where it may cause inflammation. The bioincompatibility of certain cements has also resulted in "walling off" of the prostheses, i.e., fibrous tissue forms between the host bone and the prosthesis, which may eventually weaken the junction.

Some prostheses in use, especially certain hip replacements, are much larger than the degenerative tissue that needs to be replaced. Extensive portions of healthy bone are typically removed to accomodate the prosthesis.

A need remains for prostheses which are suitable for replacement of body parts comprising articulating cartilage and which avoid problems associated with prior art prostheses, such as those discussed above.

SUMMARY OF THE INVENTION

We have found that differential demineralization of a bone segment can be used to produce a prosthesis inuseful for replacement of articular cartilage. The bone segment is advantageously machined into the desired size and shape. A portion of the bone segment is demineralized (which imparts a "spongy" texture) and serves as the actual cartilage replacement, while a non-demineralized portion becomes incorporated into the host bone, thus anchoring the prosthesis in place. The use of cements to attach the prosthesis to host bone is thus avoided. The bone is tanned to produce a biocompatible, non-antigenic, and stabilized material.

DETAILED DESCRIPTION OF THE INVENTION

Figure 2:
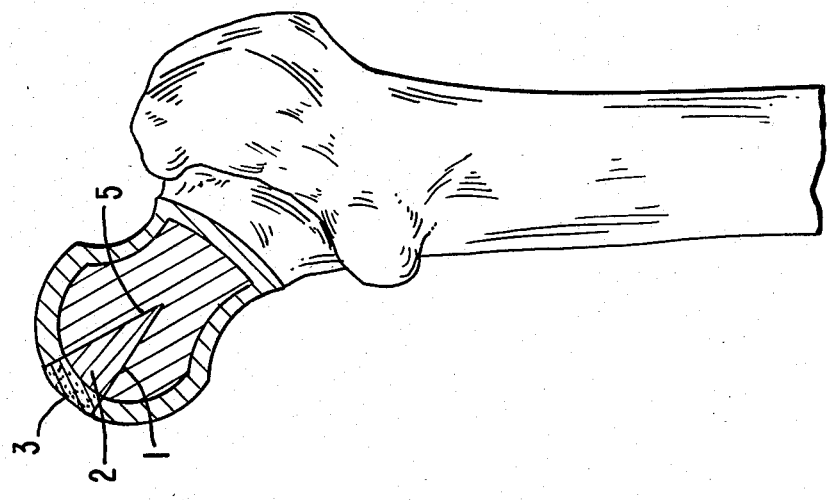
FIG. 2 is a cross-sectional view of a differentially demineralized bone plug produced by the method of the invention and implanted in a human femur.

The present invention provides a method of producing prostheses useful for replacement of articulating cartilage, as well as the prostheses so produced. The prostheses of the present invention have several advantages over those of the prior art, including the fact that no cement is needed to anchor them in place. The prostheses are derived from bone which can be machined into a wide variety of sizes and shapes. The bone is tanned, which yields a biocompatible, non-antigenic, and sterilized material. These advantages and others are discussed more fully below.

The prostheses have a wide range of uses, being suitable for replacement of virtually any articular cartilage which is adjacent to bone. Replacement of cartilage in any joint (such as hip, knee, and elbow joints, to name just a few) and discs in the spinal column are among the uses. In general, any prosthesis which is to be attached to host bone and which needs to have a "spongy"-textured, shock-absorbing outer surface may be produced by the method of the present invention.

The method of producing the prostheses of the present invention is a multi-step process in which the order of the steps may vary. This process begins with selection of a bone source from which the prosthesis can be derived. Since later treatment with glutaraldehyde renders the bone non-antigenic by cross-linking the proteins, the bone may be taken from a wide variety of xenogenic or allogenic sources, including but not limited to such readily available sources as bovine, ovine, equine, or porcine bone. The bone source is preferably large enough so that a prosthesis of the desired dimensions can be machined from it in one piece.

The bone stock is obtained fresh, and the desired section is grossly removed by any suitable means such as cutting with a saw. The bone is advantageously kept moist and cool (at or below physiological temperatures so bone material is not denatured) by frequent rinsing in a fluid, such as saline or distilled water. Preferably, the bone piece is taken from the condylar section of a long bone. Associated connective tissue (tendons, ligaments, and fascia) is removed. A smaller bone piece that more closely approximates the desired final prosthesis dimensions may be obtained by coring the bone piece using, for example, a hole saw. The bone piece may again be rinsed and cooled with fluid during the sawing and afterward to remove debris.

Any conventional means of machining hard materials, including the use of drills, lathes, saws, and other tools, may be used to obtain the desired final prosthesis shape from the bone piece. Advantageously, the size and shape of the final prosthesis will conform to the dimensions of the damaged cartilage to be replaced, and will additionally comprise a portion to be placed adjacent to host bone to anchor the prosthesis. This "anchoring portion" may have a shape that fits into a matching recess cut into the host bone during surgery. The anchoring process is described below. Thus, prostheses conforming to the exact pre-determined dimensions of a damaged or degenerative area to be replaced can be produced, so that only a minimal amount of adjacent healthy bone or cartilage is removed before installing the prosthesis. In addition, the surgeon does not need to mold or otherwise shape the prosthesis of the present invention during surgery. However, at the surgeon's option, it may be tailored to more exacting dimensions. By contrast, certain known prostheses currently in use (certain hip prostheses, for example) require resection of large sections of healthy host bone before the prosthesis is attached.

Following the machining steps above, the bone piece is surface cleaned to remove machine oils and debris. Any suitable solvent may be used, and a preferred surface-cleaning method involves submersion of the bone piece in 100% ethanol followed by saline rinses. The ethanol also surface defats the material.

Portions of the shaped bone piece are demineralized in a differential demineralizing step. The portion to be demineralized is the prosthesis portion that is to serve as the "spongy"-textured cartilage replacement or shock absorbing cushion. The remaining portion of the bone piece will be positioned adjacent to or fitted into resected host bone. The host bone will grow into this non-demineralized portion of the prosthesis, thus anchoring it in place without using cements. Wires, screws, external fixation devices, or other suitable means of attachment may be used to position the prosthesis until the host bone has invaded the non-demineralized portion to a degree sufficient to anchor it. The wires and/or screws may then be removed or may be left in place.

The differential demineralization may be accomplished by any effective method. For example, the cartilage-replacing portion of the bone piece may be submerged in any effective demineralizing solution. The demineralizing solution may comprise an organic or mineral acid, including but not limited to HCl, and/or a suitable $Ca^{++}$ chelator such as EDTA. Preferably, the demineralizing solution comprises abut 0.1N to 1.0N HCl, most preferably 0.3N HCl. Advantageously, the demineralizing solution also comprises up to 1% EDTA, preferably 0.1% EDTA. The remaining portion of the bone piece is submerged in a non-demineralizing solution such as physiological saline. The container into which the bone piece is placed during this differential demineralization may vary in design according to the size and shape of the prosthesis. Generally, the container will have two compartments, one for the demineralizing solution and another for the non-demineralizing solution. Any non-diffusable barrier (steel, glass, plastic, etc.) may separate the compartments. The bone piece is secured in an opening in the barrier so that the appropriate portion of the bone piece is submerged in each solution. Hydrostatic pressure (i.e., positive pressure exerted by the non-demineralizing solution diffusing into the prosthesis) keeps the demineralizing solution from diffusing throughout the prosthesis, thus limiting the location of demineralization.

The extent of demineralization can be monitored by any suitable means, including X-ray analysis or simply checking the feel at regular intervals, and is stopped when the desired portion of the bone piece is sufficiently demineralized (i.e., when it has the desired consistency). The result is a bone piece with both substantially demineralized and non-demineralized portions. In addition, a zone of intermediate demineralization may be present at the interface.

Advantageously, the prosthesis has an "axis of compression" that is parallel to the sagittal plane of the bone from which it was derived. As used herein, "axis of compression" refers to the direction in which force will be exerted upon the demineralized portion of the prosthesis once implanted. The demineralized portion of a prostheses machined from bone in the desired orientation has a spongy texture that "springs back" when compressed and thus has shock-absorbing properties. Prostheses machined in other orientations with respect to the bone stock will have demineralized portions that are spongy but which may collapse (rather than springing back) when compressed.

Advantageously, the bone piece is treated to increase the porosity of the matrix and thus further encourage growth of host bone into the adjacent "anchoring portion" of the prosthesis. This porosity can be accomplished by extracting the bone piece with an organic solvent, such as chloroform, 100% ethanol chloroform:methanol (1:1), acetone or similar solvents, followed by rinsing in physiological saline to remove the organic solvent. Advantageously, this porosity-increasing step may include treatment of the bone piece with a protease such as Pronase ®, collagenase, or hyaluronidase (all commercially available). Preferably, the bone pieces are treated with Pronase ® and then with chloroform:methanol (1:1). This step increases the porosity by removing non-matrix-bound proteins. Desirably, all such proteins are removed. If all the non-matrix-bound proteins are removed, the matrix porosity can be increased by as much as 10%. This porosity-increasing treatment can be done before or after the differential demineralization step. Matrix integrity, porosity and desired contour can be checked by visual inspection, and the degree of porosity can be determined by light or electron microcopy.

The bone piece is tanned to provide a non-antigenic and biocompatible prosthesis. This tanning step may be done at any time during the derivation of a prosthesis of the invention. Most preferably, the tanning step is done after the differential demineralizing step. Numerous tanning procedures are known, and glutaraldehyde tanning is preferred for preparation of the prosthesis of this invention. This bone piece is treated with a tanning reagent under tanning conditions until it is rendered stable, biocompatible, and non-antigenic. Advantageously, tanning is accomplished by submersion for about one month or more in a solution comprising about 0.2% to 0.8%, preferably about 0.6% (w/v), glutaraldehyde in a suitable buffer such as HEPES, having a pH of about 6.8 to 7.5. The process may be monitored by any suitable method, including a colorimetric assay using, for example, a ninhydrin reaction (a colorimetric assay for amino groups in which the color intensity will decrease as the cross-linking increases). The glutaraldehyde treatment imparts many desirable properties to the prosthesis. For example, cross-linking of proteins by glutaraldehyde renders the prosthesis non-antigenic so that the prosthesis may be implanted in a host other than the one from which the stock bone was taken to produce it.

Glutaraldephyde-treated bone has been found to have, excellent biocompatibility. When glutaraldehyde-treated non-demineralized bone is implanted in host bone in mammals, there is generally no fibrous encapsulation, interposition of fibrous tissue between host bone and implanted bone, or other evidence of host rejection. Instead, the host bone grows into the adjacent implanted bone. This host bone ingrowth is termed osteoinvasion or osteoconduction.

Glutaraldehyde tanned and demineralized bone which has been implanted in host bone in mammals, remains soft and demonstrates good biocompatibility. By contrast, interposition of fibrous tissue and encapsulation are known to occur when implants made of less biocompatible materials are introduced into mammals.

One problem associated with prosthesis use is degeneration of the prosthesis, which often necessitates replacement. The degenerating material may also migrate and cause problems such as inflammation in the host. The long-term stability imparted to the prostheses of the present invention by glutaraldehyde tanning will solve such problems.

Resorption of implanted bone-derived material is known to occur. The resorbed material may or may not be replaced by the host. In some cases, it may be desirable to implant a prostheses that is resorbed as host tissue replaces it. In such a case, the glutaraldehyde tanning step could be replaced by tanning with different agents (e.g., formaldehyde or alcohols) that would render the material resorbable. In most cases, however, it is desirable that the implanted prostheses or template retain its shape and not be resorbed. The cross-linking that occurs during glutaldehyde treatment produces a stabilized collagen matrix in prostheses produced according to the method of the invention, and the prostheses will not be resorbed. This stable matrix (or "scaffold") is generally structurally similar to the host bone's natural matrix.

Following glutaraldehyde tanning, the bone piece may be further sterilized by any suitable means, including radiation or immersion in ethanol or a bacteriocidal solution. Preferably, a buffered surfactant/formaldehyde/ethanol sterilant is used.

The prostheses are then stored in a suitable solution such as 0.05% (w/v) glutaraldehyde in HEPES buffer, in sterile containers until needed. Before implantation, the prostheses will be rinsed with a fluid such as saline until residual glutaraldehyde levels (measurable by HPLC) have declined to a non-toxic level.

Surgical implantation of a prosthesis of the invention involves removal of the damaged portion of the host tissue and resection of host bone to expose the surface against which the prosthesis will be placed. The host bone may be resected to leave a surface which conforms to the surface of the non-demineralized portion of the prosthesis. The "spongy" demineralized portion of the prosthesis will be on the opposite side, and will not be attached to host bone. Optionally, the host bone may be resected so that the damaged tissue is removed and a recess (for example, in the shape of a cone, wedge, or cylinder) is cut into the underlying bone. A prosthesis machined so that the non-demineralized portion has a shape complementary to the recess is then fitted into the host bone. One skilled in the art will recognize the wide variety of shapes of prostheses that can be designed to be complementary to resected bone. Wires, screws, external fixation devices or other means of attachment may be used for the initial attachment of the prosthesis to the host bone. The host bone subsequently invades the non-demineralized portion of the prosthesis (the portion which is in contact with the host bone). Growth of host bone into adjacent implanted bone that was not demineralized but was tanned with glutaraldehyde and otherwise processed as described above has been demonstrated in animal studies, as discussed above. The tanned and demineralized portion of the prosthesis is not in direct contact with host bone and will not be invaded by host bone but, rather, retains its soft and "spongy" texture. In animal studies, glutaraldehyde-tanned and demineralized bone has been implanted in host bone, and retained its soft texture.

Figure 1:
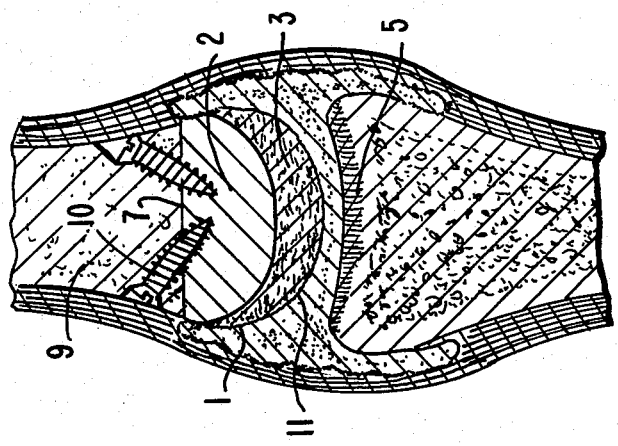
FIG. 1 is a cross-sectional view of a differentially demineralized prosthesis which has been implanted in a human synovial joint.

Specific applications of the prostheses of this invention are illustrated in FIGS. 1 and 2. FIG. 1 is a cross sectional view of a human synovial joint in which a prosthesis has been implanted. The prosthesis 1 has been machined from a condylar section of bovine bone to have a flat surface 7 and an outer convex surface 11 corresponding to the shape of the host bone being replaced. The prosthesis comprises a non-demineralized portion 2 and a demineralized portion 3 which replaces the damaged or diseased articular cartilage of the host and which provides a spongy cushion to mate with the articular cartilage 5 of the opposing bone surface. The surgeon implants the prosthesis by removing the end of host bone 9 to leave a flat surface conforming to surface 7 of the prosthesis. The prosthesis is initially joined to host bone 9 with the aid of surgical screws 10. After the host bone has grown into the non-demineralized portion of the prosthesis and anchors it, screws 10 may be removed if desired.

FIG. 2 is a cross-sectional view of a different embodiment of the prostheses of this invention, depicting a cross sectional view of the anterior end of a human femur in which a prosthesis 1 has been implanted. The prosthesis has been machined from a condylar section of bovine bone into the shape of a cone with an outer convex surface conforming to the shape of the host bone articular cartilage being replaced. The prosthesis comprises a non-demineralized portion 2 and a demineralized portion 3, with the latter portion replacing the damaged or diseased articular cartilage of the host bone. The surgeon implants the prosthesis after cutting a complementary cone shapes into the host bone. A surgical pin or screw (not shown) can be used to secure the prosthesis until substantial host bone ingrowth has occurred.

Variations in processing the tanned bone material are within the scope of this invention. For example, the bone stock may be pulverized, resuspended in a moldable carrier (including but not limited to gelatins or polysaccharides) and cast or molded into the desired shape by known techniques rather than being machined from a single piece of bone. The resuspended pulverized bone may solidify to the desired consistency upon (or after) molding or casting. The finished prosthesis will thus be molded or cast in layers from 2 types of material: pulverized and demineralized bone, which comprises the "spongy" portion, and pulverized undemineralized bone, which comprises the "anchoring portion".

Many of the desirable properties of prostheses of the present invention have been described above. In addition, it should be noted that the prostheses are derived from a material that is not only biocompatible but hard enough to be shaped, by standard machining techiques, to any desired specifications. The machined bone can retain intricate shapes throughout the remainder of the processing. The demineralized portion retains the desired shape even though it has been rendered flexible and "spongy" in texture.

The method of producing a prosthesis of the present invention is illustrated by the following Example. One skilled in the art will recognize the variations in order of steps, prosthesis shape, and other aspects of the method of the invention and the prostheses so produced, which are within the scope of the invention. Thus, the Example is meant to illustrate, but not limit, the invention.

EXAMPLE I

Production of Machined Bone-Derived Differentially Demineralized Prosthesis for Use in Articular Cartilage Repair This example describes the preparation of a differentially-demineralized "bone-plug" such as that shown in FIG. 2. This cone-shaped plug can be fitted into a complementary recess cut into the host bone (e.g., the anterior end of the femur). The demineralized portion of the plug replaces part of the host bone's articulating cartilage in the region that will fit into the "socket" of the illium to form the hip joint.

Bone plates are cut from fresh deskinned and dehooved bovine hind legs provided by an abattoir. The bone plate is cut anterior to the ankle-tibia joint, in the region of the epiphyseal plate extending anteriorly approximately 1 ½ to 2 inches. Generally some soft marrow region is included. The associated connective tissue (tendons, ligaments and fascia) are removed prior to transfer to a machine shop, where the bone plates are frozen at 0° C. until processed.

A bone plate is selected that will yield at least a ⅜" bone piece devoid of the epiphyseal plate. It is installed in a drill press vice with either the anterior or posterior end toward the corer. The bone is cored using a ⅜" lengthened carbide tipped hole saw. Distilled water or saline is used to cool and flush the bone as it is being cored. The drill is run at 480 rpm and is advanced so as not to burn or bind in the bone as it is being cored. Care is taken when approaching the epiphyseal plate region not to break the bone core in this region. The drill is advanced slowly in this region with copious amounts of water or saline to keep the bone cool and well flushed. Once the entire plate is cored, the hole saw is removed and the bone core removed by tapping it out with a drift. The remnant bone plate is discarded.

Selected bone plugs are rinsed in 0.9% saline prior to machining. The scrap end is used to chuck in a lathe. Using a lathe that has been degreased with aerosol freon, the core is tapered to the desired dimension. The bone plug is then removed from the lathe and installed in a collet for machining of the desired articular contour. The tapered, machined bone plug is then reinstalled into the lathe and the machined end cut off.

Ethanol is then used to surface clean the bone plugs. Two liters of 100% ethanol are used for approximately 150 bone cores. The plugs are submerged in the alcohol for ½ hour and after the first half hour the alcohol is replaced with fresh 100% ethanol for an additional ½ hour. The alcohol is kept at room temperature (approximately 25° C.). The second alcohol rinse is poured off and the bone plugs are rinsed in 0.9% normal saline. Initially a quick rinse is used to clean the exterior of the plugs and container. This is followed by two 30-minute rinses in 0.9% saline. The cores are stored in buffered saline or frozen until differentially demineralized.

The articular contoured end of each bone plug is immersed in a demineralizing solution (0.3N HCl with 0.1% EDTA) for the length of time sufficient to demineralize that portion of the bone plug. The progress of the demineralizastion process can be checked by feeling the articular contoured end intermittently until the desired spongy consistency is reached. The extent of demineralization can be verified by X-ray analysis. The gradient of decalcification is maintained by the depth of submersion and by hydrostatic (positive) pressure on the opposite end, which is immersed in a non-decalcifying solution (buffered normal saline). When the desired portion of the bone plug has been demineralized, it is rinsed in buffered normal saline.

To increase matrix porosity by removing non-collagenous proteins, the plugs are next submerged in a buffered Pronase ® solution at 37° C. for 24 hours followed by rinsing in buffered normal saline. The plugs are then submerged in chloroform:methanol (1:1) for one hour with constant stirring at 25° C. in a minimum volume ratio of 20 ml/plug. Rinsing in buffered normal saline then removes the solvent. The plugs are visually inspected for matrix integrity, porosity, and the desired dimensions. Acceptable bone plugs are then tanned by submersion in 0.625% (w/v) glutaraldehyde in HEPES buffer, pH 6.8 to 7.4, for a minimum of one month.

The plugs are then sterilized in a 4% formaldehyde/22.5% ethanol/1.2% Tween 80 ® solution buffered with HEPES, pH 7.4, for a minimum of eight hours and a maximum of 24 hours at 37° C. Sterilized plugs are rinsed (four 10-minute rinses and one 6-hour rinse) and stored until needed in 0.05% (w/v) HEPES-buffered glutaraldehyde. The prosthesis will be rinsed with normal saline to reduce glutaraldehyde levels to non-toxic levels prior to implantation.

We claim:

1. A method of producing a prosthesis for replacing articular cartilage comprising:
   (a) machining a bone segment into a desired shape,
   (b) differentially demineralizing said bone segment to produce both demineralized and non-demineralized portions of said bone segment, such that demineralized portion has a spongy texture similar to natural cartilage, and the non-demineralized portion is a matrix into which adjacent host bone grows,
   (c) tanning said bone segment to render it non-antigenic, biocompatible and stable.

2. The method of claim 1 additionally comprising extracting the bone segment with an organic solvent to increase matrix porosity.

3. The method of claims 1 or 2 additionally comprising treating the bone segment with a protease to increase the matrix porosity.

4. The method of claims 1, or 2 additionally comprising a final step of sterilizing the prosthesis.

5. The method of claim 1, wherein the bone segment is tanned with glutaraldehyde under tanning conditions.

6. The method of claim 1, wherein the bone segment is differentially demineralized by
   (a) immersing one portion of the bone segment in a demineralizing solution,
   (b) immersing the remaining portion in a non-demineralizing solution such that positive pressure exerted by diffusion of the non-demineralizing solution into the bone segment keeps the demineralizing solution from diffusing throughout the bone segment.

7. The method of claim 1, wherein a portion or the bone segment is demineralized by contacting said bone segment with a demineralizing solution comprising an acid.

8. The method of claim 7 wherein said demineralizing solution additionally comprises EDTA.

9. The method of claim 1 which additionally comprises submerging the bone segment in ethanolto surface defat it and to remove machine oils and debris.

10. The method of claim 1 wherein the bone segment is derived from the condylar region of an allogenic or xenogenic bone comprising bovine, porcine, ovine, or equine long bone.

* * * * *